US007052484B2

(12) United States Patent
Veasey et al.

(10) Patent No.: US 7,052,484 B2
(45) Date of Patent: May 30, 2006

(54) DRIVE MECHANISM FOR AN INJECTION DEVICE

(76) Inventors: Robert Frederick Veasey, 35 Hitchman Rd., Leamington Spa (GB) CV31 1QH; Robert Woolston, 3 Chestnut Grove, Moreton Morrell, Warwick (GB) CV35 9DG; Christopher Nigel Langley, 120 Leicester Lane, Leamington Spa, Warwickshire (GB) CV32 7HH; Shane Alistair Day, 9 Brese Avenue, Warwick (GB) CV34 5TS ( * ) Notice: Subject to any disclaimer, the term of this patent is extended or adjusted under 35 U.S.C. 154(b) by 182 days.

(21) Appl. No.: 10/433,650

(22) PCT Filed: Dec. 21, 2001

(86) PCT No.: PCT/GB01/05741

§ 371 (c)(1),
(2), (4) Date: Jun. 6, 2003

(87) PCT Pub. No.: WO02/051474

PCT Pub. Date: Jul. 4, 2002

(65) Prior Publication Data

US 2004/0030298 A1   Feb. 12, 2004

(30) Foreign Application Priority Data

Dec. 22, 2000   (GB)   .................................... 0031466

(51) Int. Cl.
*A61M 5/00* (2006.01)
(52) U.S. Cl. .................................... 604/208
(58) Field of Classification Search ............ 604/30–34, 604/48, 500, 503, 505–509, 65–68, 118–119, 604/131, 290, 151–155, 245–254, 207–211, 604/246, 248; 128/DIG. 12, DIG. 13; 417/18–25
See application file for complete search history.

(56) References Cited

U.S. PATENT DOCUMENTS

| 4,494,098 A | * | 1/1985 | Haneda et al. ............... 335/230 |
| 4,619,646 A | | 10/1986 | Fernandez-Tresguerres Hernandez et al. |
| 4,749,109 A | | 6/1988 | Kamen |
| 4,921,487 A | | 5/1990 | Buffet et al. |
| 5,747,350 A | | 5/1998 | Sattler |
| 5,820,602 A | | 10/1998 | Kovelman et al. |
| 6,042,571 A | | 3/2000 | Hjertman et al. |

FOREIGN PATENT DOCUMENTS

| EP | 0 514 816 A1 | | 11/1992 |
| GB | 2 094 628 A | | 9/1982 |
| WO | WO97/36623 | * | 10/1997 |
| WO | WO 97/36623 | | 10/1997 |

* cited by examiner

*Primary Examiner*—Nicholas D. Lucchesi
*Assistant Examiner*—Michael M Thompson
(74) *Attorney, Agent, or Firm*—Oliff & Berridge, PLC

(57) ABSTRACT

A drive mechanism for an injection device is disclosed in which piston means 306 are selectively driven to expel medicament from within a medicament cartridge 40. A drive mechanism for controlling the movement of the piston means is described comprising a housing 302, a shuttle 300 located for movement within the housing 302 along a longitudinal axis between a first position and a second position, and drive means to move the shuttle 300 within the housing 302. A gear component 304 is located within the housing 302 for rotation about the longitudinal axis and associated with the piston means 306, movement of the shuttle 300 between each of the first and the second positions causing movement of the piston means 306.

8 Claims, 3 Drawing Sheets

DRIVE MECHANISM FOR AN INJECTION DEVICE

The present invention relates to improvements in an injection device, and in particular to improvements in a portable injection device for dispensing controlled quantities of a medicament.

Typically such injection devices are used by those suffering from diabetes to administer a dose of insulin or insulin-type medicine to themselves. It will be understood that such injection devices are suitable for the injection of other medicines.

At one time, such doses were administered by use of a disposable syringe; the syringe first being filled from a separate phial or other container and then used to inject the dose. However, there were a number of difficulties in such an arrangement. In particular, such an arrangement was not suitable for the infirm. For others, the social stigma associated with such syringes made their public use problematic.

To overcome these difficulties a number of so-called pen-type injectors have been developed. These devices are small, being capable of being carried in a jacket pocket or the like and allow a number of doses to be obtained from a cartridge or ampoule contained within the injector. The present invention has particular application to such pen-type injectors.

While such pen-type injectors are a considerable improvement upon disposable hypodermic syringes, problems nevertheless remain.

In particular when considering the design of a drive system for a pen-type injector, there are a number of, sometimes, conflicting technical requirements. The drive system must be accurate and reliable, and at the same time compact and efficient. The drive system must be reliable and robust; being able to function for the life of the product. The drive system must also be intrinsically fail-safe.

It is an advantage of the present invention that it eliminates, or at least substantially reduces such problems. The present invention also provides for improved ease of use and improved interaction with a user.

The invention will now be described, by way of example only, with reference to the accompanying drawings; in which.

Figure 1:
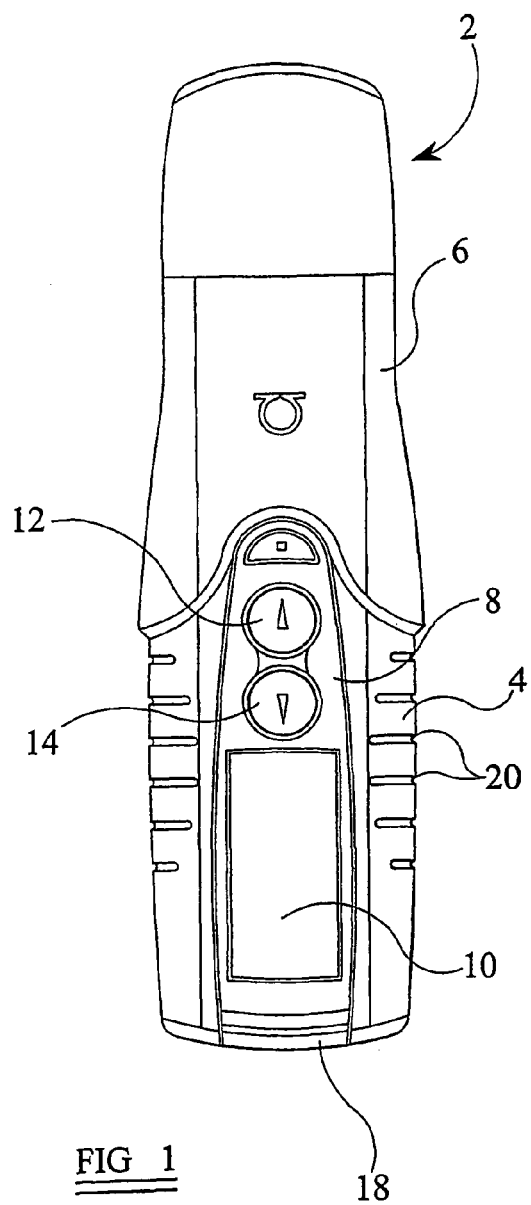
FIG. 1 shows a plan view of a pen-type injector in accordance with the present invention.
Figure 2:
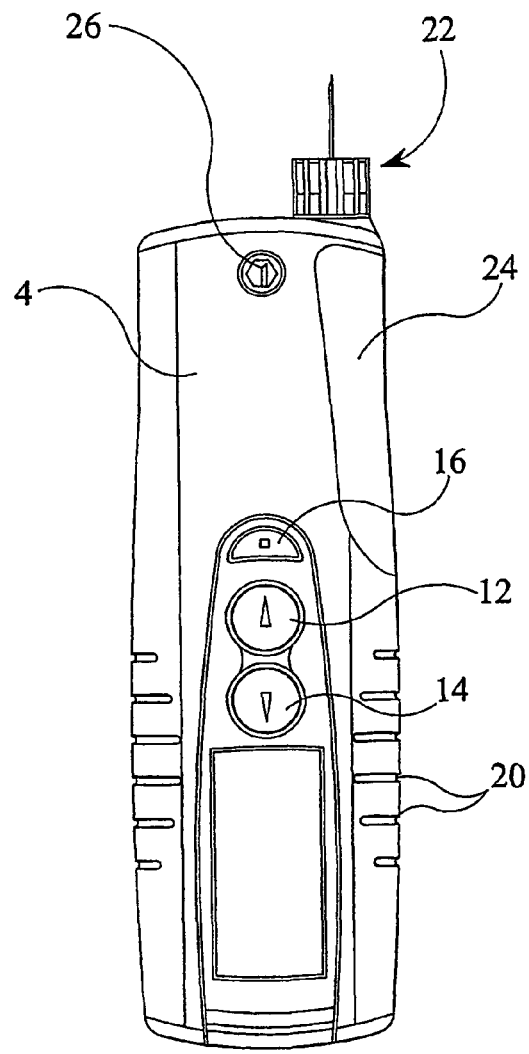
FIG. 2 shows a similar view to FIG. 1 with an end cap of the injector omitted.
Figure 3:
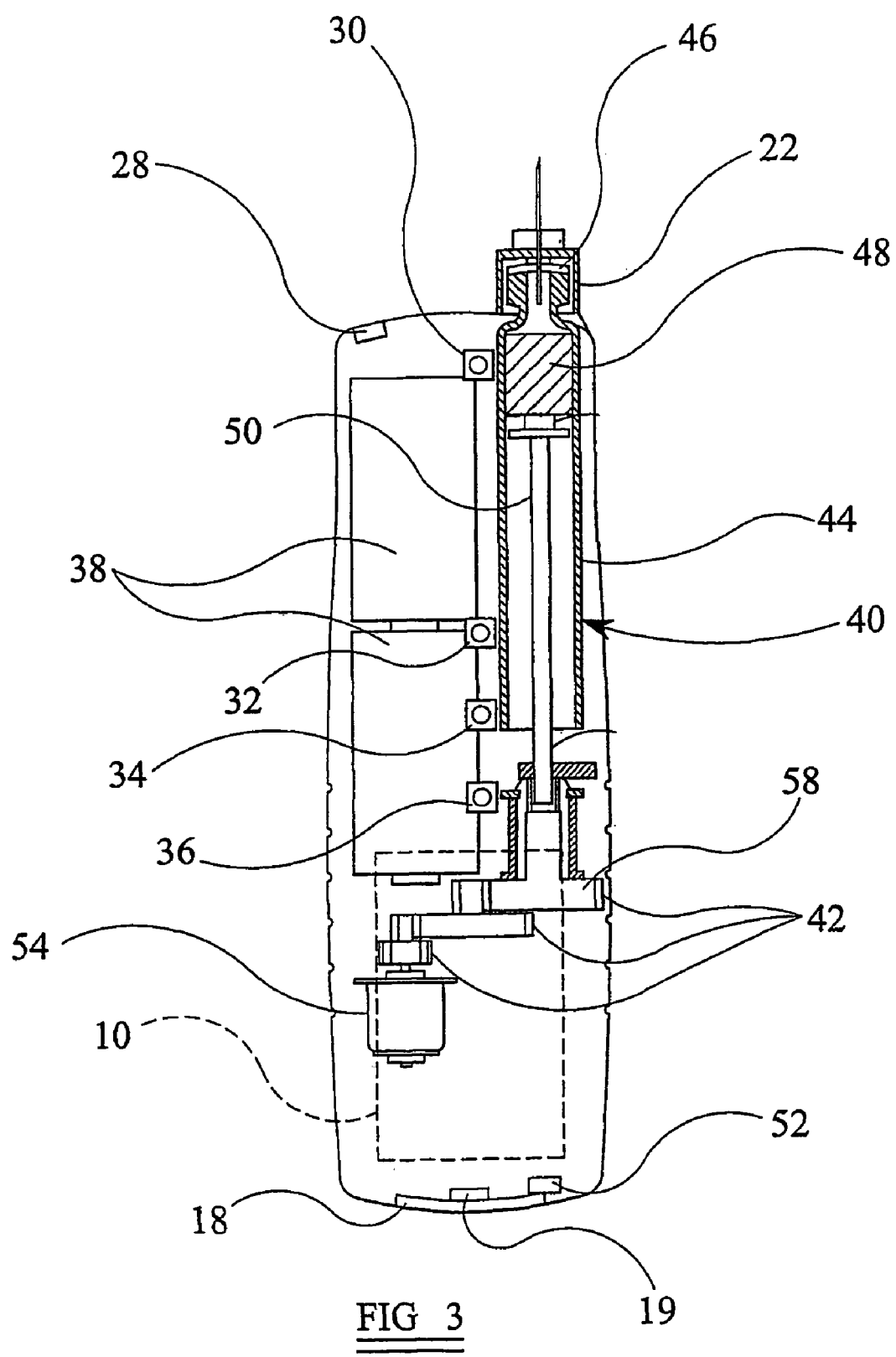
FIG. 3 shows a cross-sectional view of the injector of FIGS. 1 and 2.

Referring first to FIGS. 1 to 3, there can be seen a pen-type injector 2 in accordance with the present invention. The injector 2 comprises a main housing 4 to which is releasably secured an end cap or cover 6.

At a first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 10 in the illustrated embodiment also includes an arm button 16.

At the first end of the main housing there is also provided a dispense button 18. Preferably, when not depressed, the dispense button 18 is flush with the main housing 4.

Along a longitudinal axis of the injector 2, to each side of the control panel region 10 are provided a number of grooves or recesses 20. These aid in the gripping of the injector 2 by a user.

At a second end of the main housing 4 a needle unit 22 is releasably secured to the main housing. The second end of the main housing 4 is also provided with a shaped portion 24.

In use a cartridge 40 or ampoule of medicament is stored in the housing 4 behind the shaped portion 24. For preference, the shaped portion is transparent to permit the cartridge 40 to be seen by a user.

A primer button 26 is also provided on the second end of the housing 4. It will be understood that when the end cap 6 is in place over the second end of the housing, it will not be possible inadvertently to depress the primer button 26 or to be pricked by the needle unit 22. A cover detection switch 28 may also be included at the second end of the main housing 4 to detect whether the end cap or cover 6 is in place or not.

In FIG. 3, there can be seen a priming contact 30, an arm contact 32, a first dose contact 34 and a second dose contact 36 corresponding to the respective buttons. A dispense contact 19 corresponding to the dispense button 18 is also shown.

With reference to FIG. 3 it may be seen that there is provided a suitable location for a power source 38 such as a battery or batteries. There is also a suitable region in which a cartridge 40 or ampoule of medicament is to be located. This region may be accessed by way of the removable shaped portion 24 of the main housing 4 to allow for replacement of the cartridge 40 or ampoule as required by the user.

In a third region of the main housing 4 there is provided a drive mechanism 42 which operates from the power source 38 and acts upon the cartridge 40 or ampoule of medicament.

The cartridge 40 or ampoule comprises a container 44 or sleeve closed at one end by a cover 46 at a head end thereof, and sealed at the other by a movable bung 48 or stopper. When in position, the needle unit 22 pierces the cover 46 and movement of the bung 48 towards the cover 46 will cause the medicament contained within the cartridge 40 or ampoule to be expelled. The cartridge may be a 3 ml cartridge in accordance with ISO/FDIS 11608 Part 3, or any other suitable cartridge to suit the injector.

Movement of the bung 48 or stopper is caused by movement of a piston or plunger 50 forming a part of the drive mechanism 42. The piston or plunger 50 is movable between a first fully withdrawn position (not shown) which allows for the replacement of the cartridge 40 or ampoule and a second fully extended portion in which as much medicament as possible has been expelled from the cartridge 40 or ampoule. An end stop switch 52 may be provided in the main housing 4 to detect when the piston 50 is in the fully withdrawn position. Tripping of the switch end stop 52 may release a catch or other fastening device to allow access to the main housing 4 for replacement of the cartridge 40.

The drive mechanism 42 is operated by a motor 54 under the control of an electronic control unit (not shown). The motor 54 should be reversible in order to allow the piston 50 to be moved between the first and second positions. In FIG. 3, the motor 54 can be seen to drive the piston 50 by way of a gear train 42, such that rotation of a third rotor 58 causes the piston 50 to be moved in relation to the third rotor 58.

Preferably, the user can feel the vibration of the motor 54 and the associated drive mechanism 42 and/or hear them in operation. In this way an added degree of confidence in the fact of the operation of the injector 2 is provided to the user.

In order to harness a solenoid for use in an injector, a mechanism has been developed to convert the reciprocating motion of a solenoid into an incremental linear motion to displace a cartridge bung.

Figure 4:
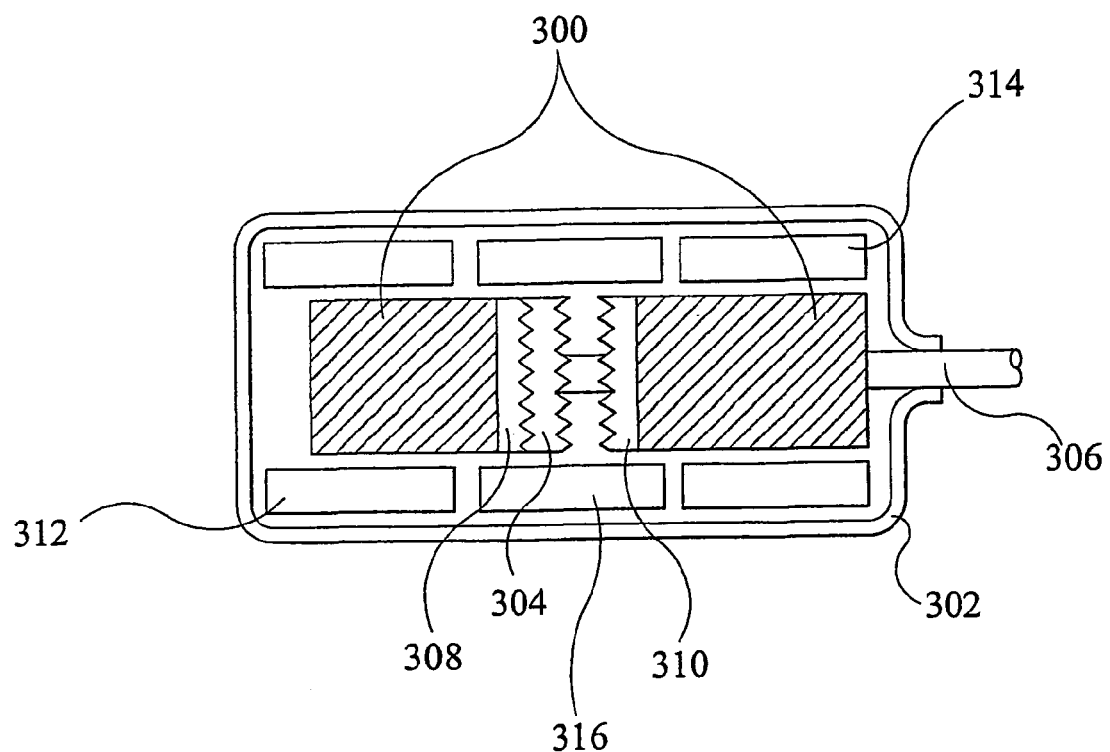
FIG. 4 shows in plan view a part of a drive mechanism for use with an injector in accordance with the present invention.

Referring to FIG. 4, a two piece shuttle 300 is constrained rotationally within a housing 302 for free axial movement therein. A double faced gear component 304 is also located within the housing. The double faced gear component 304 is free for movement rotationally, but constrained axially. The double faced gear component 304 is coupled to a shaft 306 of a lead screw. The lead screw will be understood to comprise piston means for the advancement of bung 48 within a medicament cartridge 40 within the context of this description. The shuttle comprises two ferrite cores 308,310, each with teeth on an inner face thereof. At either end the housing 302 are disposed coils 312,314. An annular permanent magnet 316 is used to latch the mechanism in one of two end positions when the cores and their associated coils are not energised.

In the de-energised condition, the shuttle 300 is held latched to one end of the device by the magnet 316. The shuttle is held in position by a closed magnetic 'circuit' passing through one of the shuttle ferrite cores and a casing of the housing 302.

In order to move the shuttle 300 to the opposite end of the housing both coils 312,314 are energised. The coil at the 'latched' end is energised to oppose the magnetic field of the permanent magnet 316; the coil at the opposite end is energised to reinforce the permanent magnetic field. The shuttle 300 is thus pulled from the rest position to the opposite end of the housing 302. In moving from one end of the housing 302 to the other, the shuttle 300 engages with the double faced gear component 304 causing it to rotate by a fixed increment, thereby turning the shaft 306 of a lead screw.

When the shuttle 300 comes to rest at the opposite end of the housing 302, it is again latched in position by the permanent magnet 316.

The mechanism can be seen to work on both strokes of the solenoid. Also, it can be latched at either end allowing for finer control of the lead screw.

What is claimed is:

1. A drive mechanism for an injection device in which piston means is selectively driven to expel medicament from within a medicament cartridge, the drive mechanism controlling movement of the piston means and comprising:
   a housing;
   a shuttle located for movement within the housing along a longitudinal axis between a first position and a second position;
   drive means for driving the shuttle to move within the housing; and
   a gear component located within the housing and arranged for rotation about the longitudinal axis, the gear component being associated with the piston means and cooperating with the shuttle such that movement of the shuttle between each of the first and the second positions causes rotation of the gear component and movement of the piston means.

2. A drive mechanism according to claim 1, wherein the drive means comprises separately energisable coils located at each end of the housing and an annular permanent magnet located between the coils acting upon the shuttle, the shuttle comprising at least one ferrite core.

3. A drive mechanism according to claim 1, wherein the shuttle and the gear component are each provided with teeth upon an annular surface thereof, and engagement of the shuttle with the gear component causes the gear component to be rotated by a fixed increment.

4. A drive mechanism according to claim 2, wherein the shuttle and the gear component are each provided with teeth upon an annular surface thereof, and engagement of the shuttle with the gear component causes the gear component to be rotated by a fixed increment.

5. A drive mechanism of a drug delivery device, the drive mechanism comprising:
   a housing;
   a drive shaft projecting from the housing and having a longitudinal axis, the drive shaft being supported for rotation within the housing about the longitudinal axis;
   a gear component located coaxial with the drive shaft within the housing and arranged for rotation about the longitudinal axis, wherein rotation of the gear component transmits rotational drive to the drive shaft;
   a shuttle located within the housing for movement between a first position and a second position along the longitudinal axis, and which engages the gear component at least one of the first position and the second position so as to cause rotation of the gear component; and
   drive means that drives the shuttle to move between the first position and the second position.

6. A drive mechanism of a drug delivery device, the drive mechanism comprising:
   a housing;
   a drive shaft projecting from the housing and having a longitudinal axis, the drive shaft being supported within the housing for axial movement along the longitudinal axis;
   a gear component located coaxial with the drive shaft within the housing, and arranged for rotation about the longitudinal axis, where rotation of the gear component transmits axial drive to the drive shaft;
   a shuttle located within the housing for movement between a first position and a second position along the longitudinal axis, and which engages the gear component at least one of the first position and the second position so as to cause rotation of the gear component; and
   drive means that drives the shuttle to move between the first position and the second position.

7. A drug delivery device that receives a medicament cartridge for delivery of medicament from within the medicament cartridge, the drug delivery device comprising:
   a piston selectively driven within the medicament cartridge to expel medicament from the medicament cartridge; and
   a drive mechanism that drives the piston, the drive mechanism comprising:
      a housing;
      a drive shaft projecting from the housing and having a longitudinal axis, the drive shaft being supported for rotation within the housing about the longitudinal axis to drive the piston;
      a gear component located coaxial with the drive shaft within the housing and arranged for rotation about the longitudinal axis, where rotation of the gear component transmits rotatational drive to the drive shaft;
      a shuttle located within the housing for movement between a first position and a second position along the longitudinal axis, and which engages the gear component at least one of the first position and the second position so as to cause rotation of the gear component; and drive means that drives the shuttle between the first position and the second position.

8. A drug delivery device that receives a medicament cartridge for delivery of medicament from within the medicament cartridge, the drug delivery device comprising:

a piston selectively driven within the medicament cartridge to expel medicament from the medicament cartridge; and a drive mechanism that drives the piston, the drive mechanism comprising:

a housing;

a drive shaft projecting from the housing and having a longitudinal axis, the drive shaft being supported for axial movement in the housing, along the longitudinal axis, to drive the piston;

a gear component located coaxial with the drive shaft within the housing and arranged for rotation about the longitudinal axis, where rotation of the gear component transmits axial drive to the drive shaft;

a shuttle located within the housing for movement between a first position and a second position along the longitudinal axis, and which engages the gear component at least one of the first position and the second position so as to cause rotation of the gear component; and drive means that drives the shuttle between the first position and the second position.

* * * * *